(12) United States Patent
Takatani et al.

(10) Patent No.: US 11,417,472 B2
(45) Date of Patent: Aug. 16, 2022

(54) ELECTROLYTIC CAPACITOR AND MANUFACTURING METHOD OF ELECTROLYTIC CAPACITOR

(71) Applicant: Panasonic Intellectual Property Management Co., Ltd., Osaka (JP)

(72) Inventors: Kazuhiro Takatani, Hyogo (JP); Akito Nakamura, Aichi (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/910,955

(22) Filed: Jun. 24, 2020

(65) Prior Publication Data
US 2020/0411251 A1 Dec. 31, 2020

(30) Foreign Application Priority Data
Jun. 28, 2019 (JP) .............................. JP2019-122225

(51) Int. Cl.
*H01G 9/025* (2006.01)
*H01G 9/00* (2006.01)
*C07C 309/44* (2006.01)
*C08K 5/08* (2006.01)
*H01G 9/15* (2006.01)

(52) U.S. Cl.
CPC .......... *H01G 9/025* (2013.01); *C07C 309/44* (2013.01); *C08K 5/08* (2013.01); *H01G 9/0036* (2013.01); *H01G 9/15* (2013.01)

(58) Field of Classification Search
None
See application file for complete search history.

(56) References Cited

U.S. PATENT DOCUMENTS

| | | | |
|---|---|---|---|
| 6,351,370 B1 * | 2/2002 | Konuma | H01G 9/025 361/523 |
| 10,074,490 B2 * | 9/2018 | Chacko | H01G 9/035 |
| 2004/0231119 A1 * | 11/2004 | Brenneman | H01G 9/15 29/25.03 |
| 2010/0039751 A1 * | 2/2010 | Oohata | H01G 9/042 361/523 |
| 2010/0265634 A1 * | 10/2010 | Freeman | H01G 11/56 361/529 |
| 2011/0149477 A1 * | 6/2011 | Summey | H01G 9/012 361/528 |
| 2012/0044615 A1 * | 2/2012 | Takahashi | H01G 9/028 361/528 |
| 2014/0185192 A1 * | 7/2014 | Sugawara | H01G 9/15 361/523 |

(Continued)

FOREIGN PATENT DOCUMENTS

JP 2015-017230 A 1/2015

*Primary Examiner* — Dion R. Ferguson
(74) *Attorney, Agent, or Firm* — McDermott Will & Emery LLP (57) ABSTRACT

An electrolytic capacitor including an anode body having a dielectric layer, and a solid electrolyte layer. The solid electrolyte layer contains an electrically conductive material, and an additive. The conductive material contains a π-conjugated polymer, and a polymer dopant doped in the π-conjugated polymer and having a first anionic group. The additive includes a quinone compound having a second anionic group.

7 Claims, 2 Drawing Sheets

(56) References Cited

U.S. PATENT DOCUMENTS

| | | | |
|---|---|---|---|
| 2014/0211372 A1* | 7/2014 | Sugawara | C08L 65/00 361/525 |
| 2015/0138695 A1* | 5/2015 | Tanaka | H01G 9/15 361/525 |
| 2016/0240323 A1* | 8/2016 | Chacko | H01G 11/04 |
| 2017/0169957 A1* | 6/2017 | Naito | H01G 9/07 |
| 2017/0294273 A1* | 10/2017 | Andoralov | H01G 11/30 |
| 2020/0279692 A1* | 9/2020 | Fukui | H01G 9/028 |

* cited by examiner

ELECTROLYTIC CAPACITOR AND MANUFACTURING METHOD OF ELECTROLYTIC CAPACITOR

CROSS REFERENCE TO RELATED APPLICATION

The present application is based on and claims priority under 35 U.S.C. § 119 with respect to the Japanese Patent Application No. 2019-122225 filed on Jun. 28, 2019, of which entire content is incorporated herein by reference into the present application.

TECHNICAL FIELD

The present invention relates to an electrolytic capacitor including a solid electrolyte layer and a manufacturing method of the same.

BACKGROUND

An electrolytic capacitor includes an anode body having a dielectric layer, and a solid electrolyte layer formed so as to cover at least part of the dielectric layer. The solid electrolyte layer contains a π-conjugated polymer and a dopant doped in the π-conjugated polymer. Dopants that have been widely used are polymer organic acids, such as polystyrene sulfonic acid, capable of exhibiting high electrical conductivity and low equivalent series resistance (ESR), as disclosed in Patent Document 1 (JP 2015-17230 A).

The electrolytic capacitor is often exposed to high temperatures, for example, by heat generated when ripple current flows or by heat applied during reflow soldering. Exposure to high temperature of the electrolytic capacitor leads to deterioration of the solid electrolyte layer, which may cause the ESR to increase.

SUMMARY

One aspect of the present invention relates to an electrolytic capacitor including an anode body having a dielectric layer, and a solid electrolyte layer, the solid electrolyte layer containing an electrically conductive material, and an additive, the electrically conductive material containing a π-conjugated polymer, and a polymer dopant doped in the π-conjugated polymer and having a first anionic group, the additive including a quinone compound having a second anionic group.

Another aspect of the present invention relates to a manufacturing method of an electrolytic capacitor, the method including: a first step of preparing an electrically conductive material containing a π-conjugated polymer and a polymer dopant doped in the π-conjugated polymer and having a first anionic group; a second step of preparing a processing liquid containing the electrically conductive material and a quinone compound having a second anionic group; and a third step of forming a solid electrolyte layer by impregnating the processing liquid into at least part of a dielectric layer of an anode body.

According to the present invention, an electrolytic capacitor having excellent heat resistance can be provided.

DETAILED DESCRIPTION

[Electrolytic Capacitor]

An electrolytic capacitor according to an embodiment of the present invention includes an anode having a dielectric layer, and a solid electrolyte layer. The solid electrolyte layer is formed on the dielectric layer, and contains an electrically conductive material and an additive. The conductive material contains a π-conjugated polymer, and a polymer dopant having a first anionic group. The polymer dopant is doped in the π-conjugated polymer. The additive includes a quinone compound having a second anionic group (hereinafter simply referred to as the quinone compound). The quinone compound may not necessarily be doped in the π-conjugated polymer. Usually, there is a limit to the amount of the dopant that can be doped in the π-conjugated polymer. Therefore, there may be a case where the sites that can interact with the dopant in the π-conjugated polymer is saturated with the polymer dopant having a first anionic group.

By containing the quinone compound in the solid electrolyte layer, the deterioration of the solid electrolyte layer caused when the electrolytic capacitor is exposed to high temperatures can be suppressed, and thus an increase in ESR associated with the deterioration can be suppressed. Although the detailed reason is not clear, this is presumably because the presence of the quinone compound in the vicinity of the conductive material in the solid electrolyte layer serves to prevent de-doping of the polymer dopant from the π-conjugated polymer.

The conductive material containing the polymer dopant advantageously has high electrical conductivity and low ESR. In view of securing a sufficient amount of conductive material in the solid electrolyte layer, the amount of the quinone compound contained in the solid electrolyte layer is desirably a minimum that can prevent the de-doping of the polymer dopant. That is, in the solid electrolyte layer, the amount of the quinone compound is desirably smaller than the amount of the polymer dopant. In view of maintaining the high electrical conductivity and low ESR, the amount of the quinone compound per 100 parts by mass of the polymer dopant in the solid electrolyte layer is preferably, for example, 1 part by mass or more and 40 parts by mass or less.

The quinone compound is contained in the solid electrolyte layer preferably in an amount of, per 100 parts by mass of the conductive material, for example, 0.1 parts by mass or more and 35 parts by mass or less, preferably 1 part by mass or more and 30 parts by mass or less, more preferably 5 parts by mass or more and 25 parts by mass or less. When the amount of the quinone compound in the solid electrolyte layer is 1 part by mass or more per 100 parts by mass of the conductive material, the increase in ESR can be suppressed more effectively. When the amount of the quinone compound in the solid electrolyte layer is 30 parts by mass or less per 100 parts by mass of the conductive material, a higher electrical conductivity of the solid electrolyte layer tends to be maintained.

(Quinone Compound)

The quinone compound is an aromatic compound having a quinone structure (or a ring structure having at least two carbonyl groups).

The second anionic group of the quinone compound may be, for example, a sulfonic acid group, a carboxy group, a phosphoric acid group, or a phosphonic acid group. The quinone compound may have one kind or two or more kinds of second anionic groups. A preferred second anionic group is a sulfonic acid group. Also preferred is a combination of a sulfonic acid group and an anionic group other than the sulfonic acid group. For example, the quinone compound may be a monosulfonic acid, a disulfonic acid, or a trisulfonic acid.

Examples of the quinone compound include an anthraquinone compound, a naphthoquinone compound, and a benzoquinone compound. The quinone compound is preferably an anthraquinone compound. One quinone compound may be used singly, or two or more quinone compounds may be used in combination.

The anthraquinone compound is preferably an anthraquinone compound having a sulfonic acid group, and may be, for example, a compound having a structure represented by the following general formula (1).

[Chemical formula 1]

(1)

At least one of $R^1$ to $R^8$, or at least one of $R^1$ to $R^4$ and at least one of $R^5$ to $R^8$ in the formula (1) represents a sulfonic acid group. In $R^1$ to $R^8$, the groups other than the sulfonic acid group are each independently hydrogen atom or a substituent other than hydrogen atom. Examples of the substituent include halogen atom, a hydroxyl group, an amino group, an alkyl group, an alkoxy group, and an alkylamino group. The alkyl group (including an alkyl group in an alkoxy group and an alkylamino group) has, for example, 1 to 5 carbon atoms. The alkylamino group may be a monoalkylamino group or a dialkylamino group. Some of the hydrogen atoms in the alkyl group may be replaced with halogen atom or the like.

Specific examples of the anthraquinone compound having a sulfonic acid group include anthraquinone-1-sulfonic acid, anthraquinone-2-sulfonic acid, anthraquinone-2,6-disulfonic acid, anthraquinone-2,7-disulfonic acid, anthraquinone-1,5-disulfonic acid, and 2-methylanthraquinone-6-sulfonic acid. Preferred among them are anthraquinone-1-sulfonic acid, anthraquinone-2-sulfonic acid, anthraquinone-2,6-disulfonic acid, anthraquinone-2,7-disulfonic acid, and anthraquinone-1,5-disulfonic acid.

The naphthoquinone compound is preferably a naphthoquinone compound having a sulfonic acid group, and may be, for example, a compound having a structure represented by the following general formula (2).

[Chemical formula 2]

(2)

At least one of $R^{11}$ to $R^{16}$ in the formula (2) represents a sulfonic acid group. In $R^{11}$ to $R^{16}$, the groups other than the sulfonic acid group are each independently hydrogen atom or a substituent other than hydrogen atom. Examples of the substituent include those exemplified for the substituent of $R^1$ to $R^8$ in the formula (1).

Specific examples of the naphthoquinone compound having a sulfonic acid group include 1,4-naphthoquinone-2-sulfonic acid and 1,2-naphthoquinone-4-sulfonic acid. Preferred among them is 1,2-naphthoquinone-4-sulfonic acid.

The benzoquinone compound is preferably a benzoquinone compound having a sulfonic acid group, and may be, for example, a compound having a structure represented by the following general formulas (3) and (4).

[Chemical formula 3]

(3)

[Chemical formula 4]

(4)

At least one of $R^{21}$ to $R^{24}$ in the formula (3) and at least one of $R^{31}$ to $R^{34}$ in the formula (4) represent a sulfonic acid group. In $R^{21}$ to $R^{24}$ and $R^{31}$ to $R^{34}$, the groups other than the sulfonic acid group are each independently hydrogen atom or a substituent other than hydrogen atom. Examples of the substituent include those exemplified for the substituent of $R^1$ to $R^8$ in the formula (1).

Preferable examples of the benzoquinone compound having a sulfonic acid group include 1,4-benzoquinone-2-sulfonic acid and 1,2-benzoquinone-4-sulfonic acid.

(π-Conjugated Polymer)

Preferable examples of the π-conjugated polymer include polypyrrole, polythiophene, and polyaniline. These may be used singly, or in combination of two or more kinds, or in the form of a copolymer of two or more kinds of monomers. By adding a quinone compound to the solid electrolyte layer containing such π-conjugated polymer, an increase in ESR can be suppressed.

Note that the polypyrrole, polythiophene, polyaniline, and the like herein each refer to a polymer whose basic skeleton is polypyrrole, polythiophene, polyaniline, or the like. Accordingly, the polypyrrole, polythiophene, polyaniline, and the like may include their derivatives. For example, the polythiophene includes poly(3,4-ethylenedioxythiophene) (PEDOT) and the like.

The π-conjugated polymer may have any weight average molecular weight of, for example, 1,000 to 100,000.

(Polymer Dopant)

Examples of the first anionic group of the polymer dopant include those exemplified for the quinone compound.

Examples of the polymer dopant include anions of polyvinyl sulfonic acid, polystyrene sulfonic acid, polyallyl sulfonic acid, poly(methallyl sulfonic acid), poly(2-acrylamide-2-methylpropane sulfonic acid), polyisoprene sulfonic acid, polyacrylic acid, and polymethacrylic acid. These may be used singly or in combination of two or more kinds. These may be in the form of a homopolymer or a copolymer of two or more monomers. Preferred among them is polystyrene sulfonic acid (PSS).

The polymer dopant may have any weight average molecular weight, preferably, for example, 1,000 to 100,000, in view of easy formation of a homogeneous solid electrolyte layer.

(Liquid Component A)

The electrolytic capacitor may include a liquid component A. The liquid component A may be used as a solvent of a later-described electrolyte. The liquid component A preferably includes a glycol compound and/or a glycerin compound (hereinafter referred to as, for example, glycol compound or the like). When the liquid component A contains the glycol compound or the like, the orientation or crystallinity of the π-conjugated polymer contained in the solid electrolyte layer is enhanced. This improves the electrical conductivity of the solid electrolyte layer and lowers the ESR of the electrolytic capacitor. Furthermore, this improves the contact between the solid electrolyte layer and the dielectric layer, leading to improved withstand voltage characteristics.

When the electrolytic capacitor is exposed to high temperatures, the liquid component, such as the glycol compound or the like, decreases, failing to sufficiently obtain an effect of improving the orientation of the π-conjugated polymer. However, in the case of adding the quinone compound in the solid electrolyte layer, even when the glycol compound or the like has decreased, the orientation of the π-conjugated polymer can be effectively maintained. Although the detailed reason is not clear, this is presumably because the quinone compound is present in the vicinity of the π-conjugated polymer and the polymer dopant even in a high temperature atmosphere. Due to the presence of the quinone compound, even though the liquid component, such as the glycol compound or the like, has decreased, the orientation of the π-conjugated polymer can be maintained. Presumably as a result, an increase in ESR is suppressed without lowering the conductivity of the solid electrolyte layer.

The ratio of the total of the glycol compound and the glycerin compound to the liquid component A is preferably 50% by mass or more, more preferably 60% by mass or more, still more preferably 70% by mass or more.

The glycol compound includes, for example, ethylene glycol, diethylene glycol, triethylene glycol, propylene glycol, and polyalkylene glycol having a molecular weight of about 190 to 400. The glycerin compound includes, for example, glycerin and polyglycerin. The degree of polymerization of the polyglycerin is preferably 2 or more and 20 or less.

The glycol compound preferably includes ethylene glycol. When the liquid component A includes two or more kinds of glycol compounds, the glycol compounds is preferably mainly composed of ethylene glycol. Ethylene glycol has a low viscosity as compared to other glycol compounds, and can easily dissolve the solute of electrolyte. Moreover, ethylene glycol is excellent in high thermal conductivity as well as in heat dissipation when ripple current flows, and therefore, is highly effective in improving the heat resistance.

The ratio of the ethylene glycol to the glycol compound is preferably 30% by mass or more, more preferably 50% by mass or more, still more preferably 70% by mass or more. The ethylene glycol may occupy 100% by mass of the glycol compound.

(Electrolyte)

The electrolytic capacitor may include an electrolyte. By using an electrolyte, an electrolytic capacitor having excellent dielectric-layer repair function can be obtained. The electrolyte contains a solvent and a solute, and the solvent may contain a liquid component A. The solute may contain an acid component and a base component. In view of suppressing the deterioration of the solid electrolyte layer, the acid component may be contained more than the base component. The molar ratio of the acid component to the base component: (acid component/base component) may be, for example, 1.0 to 10.0.

The acid component may be, for example, an organic acid, an inorganic acid, or a complex compound of an organic acid and an inorganic acid. The organic acid may be, for example, a carboxylic acid compound. Examples of the carboxylic acid compound include phthalic acid (orthoform), isophthalic acid (meta-form), terephthalic acid (paraform), maleic acid, benzoic acid, salicylic acid, toluic acid, trimeric acid, pyromellitic acid, adipic acid, enanthoic acid, malonic acid, 1,6-decanedicarboxylic acid, 1,7-octandicarboxylic acid, azeline acid, oxalic acid, and glycolic acid. Among them, phthalic acid is preferred in view of the dielectric-layer repair function and the thermal stability of the electrolyte. Examples of the inorganic acid include boric acid, phosphoric acid, phosphorous acid, hypophosphorous acid, phosphoric acid ester, carbonic acid, and silicic acid. Examples of the complex compound includes borodisalicylic acid, borodiglycolic acid, and borodioxalic acid.

The base component may be, for example, an amine compound. The amine compound may be primary, secondary or tertiary. Examples of the amine compound include methylamine, dimethylamine, trimethylamine, ethylamine, diethylamine, triethylamine, ethylenediamine, N,N-diisopropylethylamine, tetramethyl ethylenediamine, hexamethylene diamine, spermidine, spermine, amantadine, aniline, phenethylamine, toluidine, pyrrolidine, piperidine, piperazine, morpholine, imidazole, pyridine, pyridazine, pyrimidine, pyrazine, and 4-dimethylamino pyridine. These may be used singly or in combination of two or more kinds. Preferred among them are tertiary amines, such as triethylamine and monoethyldimethylamine.

The solvent may include, for example, the above-mentioned glycol compound, the above-mentioned glycerin compound, a sulfone compound, a lactone compound, and a carbonate compound. Examples of the sulfone compound include sulfolane, dimethyl sulfoxide, and diethyl sulfoxide. Examples of the lactone compound include γ-butyrolactone and γ-valerolactone. Examples of the carbonate compound include dimethyl carbonate (DMC), diethyl carbonate (DEC), ethyl methyl carbonate (EMC), ethylene carbonate (EC), propylene carbonate (PC), and fluoroethylene carbonate (FEC). These may be used singly or in combination of two or more kinds.

[Manufacturing Method of Electrolytic Capacitor]

A manufacturing method of an electrolytic capacitor according to an embodiment of the present invention includes the following first to third steps. The first step prepares an electrically conductive material containing a π-conjugated polymer and a polymer dopant doped in the π-conjugated polymer and having a first anionic group. The second step prepares a processing liquid containing the electrically conductive material and a quinone compound having a second anionic group. The third step forms a solid electrolyte layer by impregnating the processing liquid into at least part of a dielectric layer of an anode body.

According to the above manufacturing method, a solid electrolyte layer containing an electrically conductive material and a quinone compound in undoped state can be formed. The quinone compound is added after the polymer dopant is doped into the π-conjugated polymer, and therefore, the quinone compound can be contained in undoped state in the solid electrolyte layer.

(First Step)

In the first step, an electrically conductive material may be prepared as a polymer dispersion thereof. The polymer dispersion contains a liquid component B and an electrically conductive material dispersed in the liquid component B. The polymer dispersion may be a solution or a dispersion of the conductive material in the liquid component B.

The polymer dispersion may be prepared by, for example, dispersing the conductive material in the liquid component B. Also, the polymer dispersion may be prepared by the following procedures. In the liquid component B including a polymer dopant and an oxidant, a precursor monomer is polymerized, so that a π-conjugated polymer is synthesized from the precursor monomer, and the polymer dopant is doped into the π-conjugated polymer, thereby to produce particles of conductive material. The reaction solution is dialyzed to remove unreacted monomer and excess oxidant. The conductive material may be, for example, poly(3,4-ethylenedioxythiophene) (PEDOT) doped with polystyrene sulfonic acid (PSS), abbreviated as PEDOT/PSS.

The liquid component B may be water, or a non-aqueous solvent, or a mixture of water and a non-aqueous solvent. The non-aqueous solvent is not limited, and may be, for example, a protic solvent or an aprotic solvent. Examples of the protic solvent include: alcohols, such as methanol, ethanol, propanol, butanol, ethylene glycol, and propylene glycol; aldehydes, such as formaldehyde; and ethers, such as 1,4-dioxane. Examples of the aprotic solvent include: amides, such as N-methylacetamide, N,N-dimethylformamide, and N-methyl-2-pyrrolidone; esters, such as methyl acetate; and ketones, such as methyl ethyl ketone.

(Second Step)

The second step prepares a processing liquid containing, for example, the liquid component B, the conductive material, and a quinone compound. In the second step, the processing liquid may be prepared by adding a quinone compound to the polymer dispersion (liquid component B containing the conductive material) prepared in the first step. Also, the processing liquid may be prepared by adding the liquid component B containing a quinone compound to the polymer dispersion prepared in the first step.

The processing liquid contains the conductive material preferably at a concentration of, for example, 0.5 to 10 mass %. The conductive material preferably has an average particle diameter D50 of, for example, 0.01 to 0.5 μm. Here, the average particle diameter D50 is a median diameter in a volumetric particle size distribution determined by a dynamic light scattering method using a particle size distribution analyzer. The processing liquid with such concentration is suitable for forming a solid electrolyte layer in an appropriate thickness, and is easily impregnated into the dielectric layer.

(Third Step)

The third step forms a solid electrolyte layer by impregnating the processing liquid containing the conductive material and the additive into at least part of the dielectric layer. The solid electrolyte layer is formed so as to cover at least part of the dielectric layer. In the third step, the liquid component B containing the conductive material and the additive may be attached to a surface of the dielectric layer to form a film, which is followed by drying, to allow at least part of the liquid component B to evaporate from the formed film. In this way, a dense solid electrolyte layer covering at least part of the dielectric layer is formed.

A detailed description will be given below with reference to embodiments of the present invention. It is to be noted, however, that the following embodiments are not intended to limit the present invention.

Figure 1:
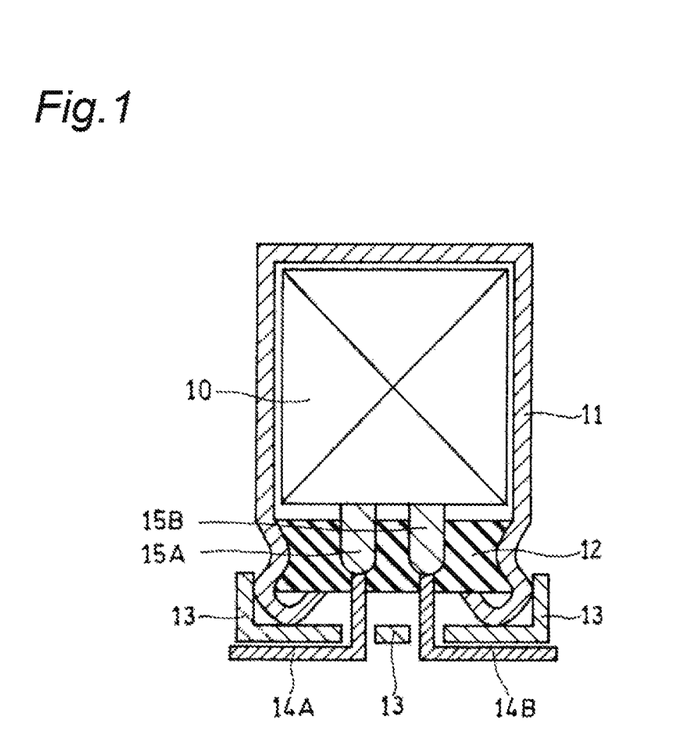
FIG. 1 is a schematic cross-sectional view of an electrolytic capacitor according to an embodiment of the present invention.
Figure 2:
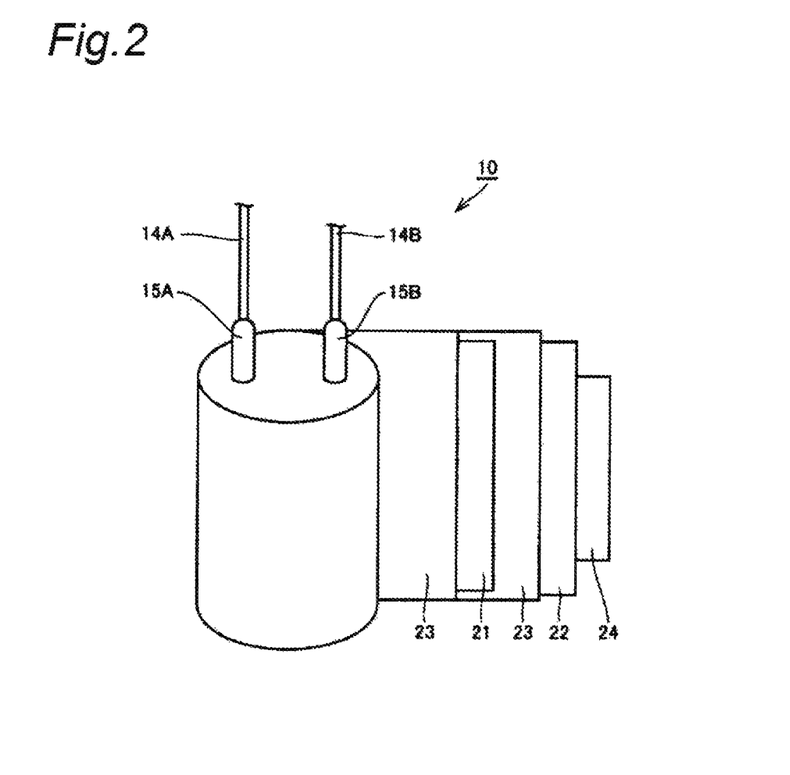
FIG. 2 is a schematic view for explaining a configuration of a capacitor element according to the embodiment.

FIG. 1 is a schematic cross-sectional view of an electrolytic capacitor according to an embodiment of the present invention, and FIG. 2 is a partially-exploded schematic view of a capacitor element according to the electrolytic capacitor.

The electrolytic capacitor includes, for example, a capacitor element 10, a bottomed case 11 housing the capacitor element 10, a sealing member 12 closing an opening of the bottomed case 11, a seat plate 13 covering the sealing member 12, lead wires 14A and 14B extending outward from the sealing member 12 and passing through the seat plate 13, lead tabs 15A and 15B connecting the lead wires to electrodes of the capacitor element 10, and an electrolyte (not shown). The bottomed case 11 is drawn inward near an edge of the opening, and the edge of the opening is bent and crimped onto the sealing member 12.

The sealing member 12 is formed of an elastic material containing a rubber component. Examples of the rubber component include butyl rubber (IIR), nitrile rubber (NBR), ethylene propylene rubber, ethylene propylene diene rubber (EPDM), chloroprene rubber (CR), isoprene rubber (IR), hyperon rubber, silicone rubber, and fluorine rubber. The sealing member 12 may additionally contain a filler, such as carbon black or silica.

The capacitor element 10 is formed of a wound body as shown in FIG. 2. The wound body is a semi-finished product of the capacitor element 10, without a solid electrolyte layer formed between an anode body 21 having a dielectric layer and a cathode body 22. The wound body includes the anode body 21 connected to the lead tab 15A, the cathode body 22 connected to the lead tab 15B, and a separator 23.

The anode body 21 and the cathode body 22 are wound, with the separator 23 interposed therebetween. The wound body is secured at its outermost layer with a stopper tape 24. FIG. 2 shows a partially-exploded view of the wound body before secured at its outermost layer.

The anode body 21 includes a surface-roughened metal foil having irregularities on its surface, and a dielectric layer is formed on the metal foil having irregularities. A solid electrolyte layer is formed by attaching an electrically conductive material on at least part of the surface of the dielectric layer. The solid electrolyte layer may cover at least part of a surface of the cathode body 22 and/or a surface of the separator 23. The capacitor element 10 including the solid electrolyte layer is housed, together with the electrolyte, in an outer case.

In the following, one example of the manufacturing method of an electrolytic capacitor according to the present embodiment will be described by each step.

(i) Step of preparing anode body 21 having dielectric layer

First, a metal foil serving as a raw material of an anode body 21 is prepared. Any kind of metal may be used, but for easy formation of a dielectric layer, preferred is a valve metal, such as aluminum, tantalum, or niobium, or an alloy including a valve metal.

Next, a surface of the metal foil is roughened. By roughening, irregularities are formed on the surface of the metal foil. The roughening is preferably performed by etching the metal foil. The etching may be performed by, for example, a direct current electrolytic process or an alternating current electrolytic process.

Next, a dielectric layer is formed on the roughened surface of the metal foil. The dielectric layer may be formed by any method, for example, by subjecting the metal foil to a chemical treatment. In the chemical treatment, the metal foil is immersed in a chemical treatment solution, such as an ammonium adipic acid solution, and, for example, heat is applied thereto, or a voltage may be applied thereto.

Typically, in view of mass productivity, a large-sized foil of valve metal (metal foil) is roughened and subjected to a chemical treatment. In this case, the treated foil is cut in a desired size, into the anode body 21.

(ii) Step of Preparing Cathode Body 22

A cathode body 22, like the anode body, may be made from a metal foil. Any kind of metal may be used, but preferred is a valve metal, such as aluminum, tantalum, or niobium, or an alloy including a valve metal. If necessary, a surface of the cathode body 22 may be roughened. On the surface of the cathode body 22A, a carbon layer, a layer of metal, such as titanium or nickel, or a layer of metal oxide layer, such as aluminum oxide or titanium oxide, may be formed.

(iii) Fabrication of Wound Body

Next, a wound body is fabricated using the anode body 21 and the cathode body 22.

First, the anode body 21 and the cathode body 22 are wound, with a separator 23 therebetween. At this time, by winding together with lead tabs 15A and 15B, the lead tabs 15A and 15B can be extended upright from the wound body as shown in FIG. 2.

The separator 23 may be made of, for example, a nonwoven fabric mainly composed of synthetic cellulose, polyethylene terephthalate, vinylon, or aramid fiber.

Next, a stopper tape 24 is attached to the outside surface of the cathode body 22 which is the outermost among the anode body 21, the cathode body 22, and the separator 23 wound together, so that the cathode body 22 is secured at its end with the stopper tape 24. In the case of using the anode body 21 prepared by cutting a large-sized metal foil, the wound body may be further subjected to the chemical treatment in order to provide a dielectric layer on the cut surface of the anode body 21.

(iv) Step of Forming Capacitor Element 10

Next, a processing liquid containing an electrically conductive material and a quinone compound is prepared, and the processing liquid is allowed to impregnate into the dielectric layer, to form a film covering at least part of the dielectric layer. As a method of supplying the processing liquid to the surface of the dielectric layer, for example, a method of immersing the wound body in the processing liquid contained in a container is simple and preferable. The immersion time is dependent on the size of the wound body, and is, for example, from 1 sec to 5 hr, preferably from 1 min to 30 min. The impregnation is preferably carried out under reduced pressure, in an atmosphere of, for example, 10 to 100 kPa, preferably 40 to 100 kPa. While immersed in the processing liquid, the wound body or the processing liquid may be applied with ultrasonic vibration. The wound body is dried after pulled up from the processing liquid, for example, at a temperature of preferably 50 to 300° C., more preferably 100 to 200° C.

The supplying of the processing liquid to the surface of the dielectric layer and the drying of the wound body may be performed twice or more. By performing these processes twice or more, the covering ratio of the dielectric layer with a solid electrolyte layer can be increased. At this time, not only the surface of the dielectric layer but also the surface of the separator 23 of the cathode body 22 may be covered with the solid electrolyte layer.

Through the above, the solid electrolyte layer is formed between the anode body 21 and the cathode body 22, and the capacitor element 10 is completed. Here, the solid electrolyte layer formed on the surface of the dielectric layer functions as the effective cathode material.

(v) Step of Impregnating Capacitor Element 10 with Electrolyte

Next, the capacitor element 10 is impregnated with an electrolyte. This provides an electrolytic capacitor having excellent dielectric-layer repair function. The method of impregnating the capacitor element 10 with the electrolyte solution is not limited. For example, a method of immersing the capacitor element 10 in the electrolyte contained in a container is simple and preferred. The immersion time is dependent on the size of the capacitor element 10, and is, for example, from 1 sec to 5 hr. The impregnation is preferably carried out under reduced pressure, in an atmosphere of, for example, 10 to 100 kPa, preferably 40 to 100 kPa.

(vi) Step of Sealing Capacitor Element

Next, the capacitor element 10 is sealed. Specifically, first, the capacitor element 10 is housed in a bottomed case 11 such that the lead wires 14A and 14B are positioned on the upper side or opening side of the bottomed case 11. The bottomed case 11 may be made of a metal, such as aluminum, stainless steel, copper, iron, brass, or an alloy thereof.

Next, a sealing member 12 configured to allow the lead wires 14A and 14B to pass therethrough is disposed above the capacitor element 10, to seal the capacitor element 10 within the bottomed case 11. Then, a lateral drawing processing is applied to the bottomed case 11 near the end of its opening, and the end of the opening is bent and crimped onto the sealing member 12. A seat plate 13 is then disposed at the bent portion. Thus, an electrolytic capacitor as shown in FIG. 1 is completed. This may be followed by aging which is performed under application of a rated voltage.

Although the above embodiment describes a wound-type electrolytic capacitor, the scope of application of the present invention is not limited thereto, and is applicable to other electrolytic capacitors, such as a chip-type electrolytic capacitor including an anode body made of a sintered body of metal, and a multilayer-type electrolytic capacitor including an anode body made of a metal plate.

EXAMPLES

The present invention will be described below in more detail with reference to Examples, but the present invention is not limited to Examples.

Example 1

A wound-type electrolytic capacitor (diameter: 10.0 mm×height: 10.0 mm) having a rated voltage of 25 V and a rated capacitance of 330 μF was produced. A detailed description will be given below of a manufacturing method of the electrolytic capacitor.

(Preparation of Anode Body)

An aluminum foil with a thickness of 100 μm was etched to roughen a surface of the aluminum foil. Then, a dielectric layer was formed on the surface of the aluminum foil by a chemical treatment. The chemical treatment was performed by immersing the aluminum foil in an ammonium adipic acid solution, to which a voltage of 45 V was applied. Thereafter, the aluminum foil was cut in a size of 8 mm wide×120 mm long, to prepare an anode body.

(Preparation of Cathode Body)

An aluminum foil with a thickness of 50 μm was etched to roughen a surface of the aluminum foil. Then, the aluminum foil was cut in a size of 8 mm wide×120 mm long, to prepare a cathode body.

(Fabrication of Wound Body)

The anode body and the cathode body were attached with an anode lead tab and a cathode lead tab, respectively, and wound together with the lead tabs, with a separator interposed between the anode body and the cathode body, to form a wound body. To the ends of the lead tabs extending from the wound body, an anode lead and a cathode lead were connected, respectively. Then, the wound body was subjected to the chemical treatment again, to form a dielectric layer at the cut end of the anode body. Subsequently, a stopper tape was attached at the end of the outermost layer of the wound body, to secure the wound body.

(Preparation of Polymer Dispersion Containing Electrically Conductive Material)

A mixed solution was prepared by dissolving 3,4-ethylenedioxythiophene, together with poly(4-styrenesulfonic acid) (PSS, weight average molecular weight: 100,000) serving as a polymer dopant, in ion-exchanged water (liquid component B). To the mixed solution under stirring, iron(III) sulfate (oxidant) dissolved in ion-exchanged water was added, to allow polymerization to proceed. The resultant reaction solution was dialyzed to remove unreacted monomers and excessive oxidant, thereby to obtain a polymer dispersion containing an electrically conductive material, poly(3,4-ethylenedioxythiophene) doped with PSS (PEDOT/PSS).

(Preparation of Processing Liquid Containing Electrically Conductive Material and Additive)

To the polymer dispersion containing the conductive material (PEDOT/PSS) obtained above, anthraquinone-2-sulfonic acid (AQS) was added as an additive in an amount of 20 parts by mass per 100 parts by mass of the conductive material, to obtain a processing liquid containing the conductive material and the additive. The amount of AQS added was 30 parts by mass per 100 parts by mass of PSS.

(Formation of Solid Electrolyte Layer)

The wound body was immersed in the processing liquid contained in a predetermined container for 5 min in a reduced-pressure atmosphere (40 kPa), and then the wound body was pulled up from the processing liquid. Next, the wound body impregnated with the processing liquid was dried in a drying oven at 150° C. for 20 min, to form a solid electrolyte layer covering at least part of the dielectric layer.

(Impregnation of Electrolyte)

A mixed solvent containing ethylene glycol (EG) as a glycol compound (liquid component A) and γ-butyrolactone (GBL) as a lactone compound in a volume ratio of 50:50 was used as an electrolyte solvent.

Phthalic acid (ortho form) serving as an organic carboxylic acid compound was used as an acid component of electrolyte solute. Triethylamine serving as an amine compound was used as a base component of electrolyte solute. The above solvent and solute were used to prepare an electrolyte.

The ratio of the solute to the whole electrolyte was 10 mass %. The molar ratio of the acid component to the base component: (acid component/base component) was 1/1. At least part of the acid component (phthalic acid) was added in a form of a salt (triethylamine phthalate) with the base component (triethylamine).

The capacitor element was immersed in the electrolyte for 5 min in a reduced-pressure atmosphere (40 kPa).

(Sealing of Capacitor Element)

The capacitor element with the electrolyte immersed therein was sealed, to complete an electrolytic capacitor. Specifically, the capacitor element was housed in a bottomed case such that the lead wires were located on the opening side of the bottomed case, and then, a sealing member (elastic material containing butyl rubber as a rubber component) configured to allow the lead wires to pass therethrough was placed above the capacitor element, so that the capacitor element was sealed within the bottomed case. Then, a drawing processing was applied near the end of the opening of the bottomed case, and the end of the opening was further bent inward. A seat plate was disposed at the bent portion. An electrolytic capacitor A1 as shown in FIG. 1 was thus completed. This was followed by aging which was performed at 130° C. for 2 hours under application of a rated voltage.

[Evaluation]

The electrolytic capacitor A1 produced above was evaluated as follows.

The electrolytic capacitor after aging was subjected to reflowing twice, each performed for 10 sec at a peak temperature of 260±5° C. The electrolytic capacitor after reflowing was measured for an ESR value (initial ESR value: X0) (Ω) at a frequency of 100 kHz, using an LCR meter in a 20° C. environment.

After the measurement of X0, a high temperature load test was performed. Specifically, at a temperature of 145° C., the rated voltage was applied to the electrolytic capacitor for 1000 hours. The electrolytic capacitor after the high-temperature load test was measured for an ESR value (X1) (Ω) in the same manner as described above.

Using the obtained X0 and X1, a ratio of increase in ESR (ΔESR) was calculated from the following formula.

$$\Delta ESR\ (\%) = (X1/X0) \times 100$$

Comparative Example 1

An electrolytic capacitor B1 was produced and evaluated in the same manner as in Example 1, except that no additive (AQS) was added to the polymer dispersion containing the conductive material (PEDOT/PSS).

Comparative Example 2

A mixed solution was prepared by dissolving 3,4-ethylenedioxythiophene, together with AQS serving as a low molecular weight dopant, in ion-exchanged water (liquid component). To the mixed solution under stirring, iron(III) sulfate (oxidant) dissolved in ion-exchanged water was added, to allow polymerization to proceed. The resultant reaction solution was dialyzed to remove unreacted monomers and excessive oxidant, thereby to obtain a polymer dispersion containing an electrically conductive material, poly(3,4-ethylenedioxythiophene) doped with AQS (PEDOT/AQS).

An electrolytic capacitor B2 was produced and evaluated in the same manner as in Example 1, except that the polymer dispersion containing the conductive material (PEDOT/AQS) was used in place of the processing liquid containing the conductive material (PEDOT/PSS) and the additive (AQS).

Comparative Example 3

A mixed solution was prepared by dissolving 3,4-ethylenedioxythiophene, together with AQS serving as a low molecular weight dopant, in ion-exchanged water (liquid component). To the mixed solution under stirring, iron(III) sulfate (oxidant) dissolved in ion-exchanged water was added, to allow polymerization to proceed. The resultant reaction solution was dialyzed to remove unreacted monomers and excessive oxidant, thereby to obtain a polymer dispersion containing a second electrically conductive material, poly(3,4-ethylenedioxythiophene) doped with AQS (PEDOT/AQS).

To the polymer dispersion containing the first conductive material (PEDOT/PSS), the second conductive material (PEDOT/AQS) was added in place of the additive (AQS). The blending ratio of the first conductive material to the second conductive material was adjusted such that the amount of AQS contained in the second conductive material was 20 parts by mass, per 100 parts by mass of the first conductive material. An electrolytic capacitor B3 was produced and evaluated in the same manner as in Example 1, except that the above.

Evaluation results of each electrolytic capacitor are shown in Table 1.

TABLE 1

| Electrolytic capacitor | Solid electrolyte layer | | ESR Initial value X0 ($\Omega$) | $\Delta$ESR (%) |
|---|---|---|---|---|
| | Conductive material | Additive | | |
| A1 | PEDOT/PSS | AQS | 0.011 | 132 |
| B1 | PEDOT/PSS | Not added | 0.018 | 175 |
| B2 | PEDOT/AQS | Not added | 0.028 | 212 |
| B3 | PEDOT/PSS and PEDOT/AQS | Not added | 0.020 | 194 |

In the electrolytic capacitor A1, the initial ESR value (X0) after reflowing was low, and the ESR value (X1) after high-temperature load test was also low, resulting in a small $\Delta$ESR. In the electrolytic capacitor A1 containing AQS in the solid electrolyte layer, the de-doping of PSS from PEDOT was suppressed, which suppressed the deterioration of the solid electrolyte layer, resulting in a suppressed increase in ESR.

In the electrolytic capacitor B1 containing no AQS in the solid electrolyte layer, the de-doping of PSS from PEDOT occurred, which led to the deterioration of the solid electrolyte layer, resulting in increased X0 and $\Delta$ESR.

In the electrolytic capacitor B2 containing PEDOT/AQS as the conductive material, the conductivity of the solid electrolyte layer was low, resulting in higher X0 and $\Delta$ESR than those of the electrolytic capacitors A1, B1, and B3.

In the electrolytic capacitor B3 containing AQS in a state of being doped in PEDOT in the solid electrolyte layer, AQS failed to act to suppress the de-doping of PSS from PEDOT, resulting in increased X0 and $\Delta$ESR.

Examples 2 to 8

Electrolytic capacitors A2 to A8 were produced and evaluated in the same manner as in Example 1, except that the additive (AQS) was added in an amount as shown in Table 2 to the polymer dispersion containing the conductive material (PEDOT/PSS). The evaluation results are shown in Table 2. In Table 2, the amount of AQS added is expressed as an amount per 100 parts by mass of the conductive material (parts by mass). Table 2 also shows the evaluation results of the electrolytic capacitors A1 and B1.

TABLE 2

| Electrolytic capacitor | Amount of AQS added (parts by mass) | ESR Initial value X0 ($\Omega$) | $\Delta$ESR (%) |
|---|---|---|---|
| B1 | 0 | 0.018 | 175 |
| A2 | 0.5 | 0.015 | 149 |
| A3 | 1 | 0.013 | 139 |
| A4 | 5 | 0.012 | 139 |
| A5 | 10 | 0.012 | 135 |
| A1 | 20 | 0.011 | 132 |
| A6 | 25 | 0.012 | 132 |
| A7 | 30 | 0.013 | 130 |
| A8 | 35 | 0.015 | 128 |

In the electrolytic capacitors A1 to A8, as compared to the electrolytic capacitor B1, the X0 after reflowing was low, and the X1 after high-temperature load test was also low, resulting in a small $\Delta$ESR. The electrolytic capacitors A3 to A7, in which the amount of AQS added was 1 to 30 parts by mass per 100 parts by mass of the conductive material, showed a further lower X0, and a small $\Delta$ESR.

Examples 9 to 15

Electrolytic capacitors A9 to A15 were produced and evaluated in the same manner as in Example 1, except that the compounds shown in Table 3 were used as the additive in place of anthraquinone-2-sulfonic acid. The evaluation results are shown in Table 3. Table 3 also shows the evaluation results of the electrolytic capacitor A1.

TABLE 3

| Electrolytic capacitor | Solid electrolyte layer | | ESR Initial value X0 ($\Omega$) | $\Delta$ESR (%) |
|---|---|---|---|---|
| | Conductive material | Additive | | |
| A1 | PEDOT/PSS | anthraquinone-2-sulfonic acid | 0.011 | 132 |
| A9 | PEDOT/PSS | anthraquinone-1-sulfonic acid | 0.011 | 133 |
| A10 | PEDOT/PSS | anthraquinone-2,6-disulfonic acid | 0.012 | 133 |
| A11 | PEDOT/PSS | anthraquinone-2,7-disulfonic acid | 0.013 | 134 |
| A12 | PEDOT/PSS | anthraquinone-1,5-disulfonic acid | 0.013 | 135 |
| A13 | PEDOT/PSS | 1,2-naphthoquinone-4-sulfonic acid | 0.011 | 133 |
| A14 | PEDOT/PSS | 1,4-benzoquinone-2-sulfonic acid | 0.014 | 135 |

TABLE 3-continued

| Electrolytic capacitor | Solid electrolyte layer | | ESR Initial value X0 ($\Omega$) | $\Delta$ESR (%) |
|---|---|---|---|---|
| | Conductive material | Additive | | |
| A15 | PEDOT/PSS | 1,2-benzoquinone-4-sulfonic acid | 0.015 | 137 |

In the electrolytic capacitors A9 to A15, like in the electrolytic capacitor A1, the X0 after reflowing was low, and the X1 after high-temperature load test was also low, resulting in a small $\Delta$ESR. Among them, in the electrolytic capacitors A1, A9, A10, and A13, the X0 was further lower, and the $\Delta$ESR was also small.

INDUSTRIAL APPLICABILITY

The present invention is applicable to an electrolytic capacitor including a solid electrolyte layer covering at least part of a dielectric layer.

REFERENCE SIGNS LIST

10: Capacitor element, 11: bottomed case, 12: sealing member, 13: seat plate, 14A, 14B: lead wire, 15A, 15B: lead tab, 21: anode body, 22: cathode body, 23: separator, 24: stopper tape

What is claimed is:

1. An electrolytic capacitor comprising an anode body having a dielectric layer, and a solid electrolyte layer,
    the solid electrolyte layer containing an electrically conductive material, and an additive,
    the electrically conductive material containing a π-conjugated polymer, and a polymer dopant doped in the π-conjugated polymer and having a first anionic group,
    the additive including a quinone compound having a second anionic group,
    wherein at least part of the quinone compound is not doped in the π-conjugated polymer.

2. The electrolytic capacitor of claim 1, wherein the solid electrolyte layer contains the quinone compound in an amount of 1 part by mass or more and 30 parts by mass or less, per 100 parts by mass of the electrically conductive material.

3. The electrolytic capacitor of claim 1, wherein the quinone compound includes at least one compound selected from the group consisting of an anthraquinone compound, a naphthoquinone compound, and a benzoquinone compound.

4. The electrolytic capacitor of claim 1, wherein the quinone compound includes at least one selected from the group consisting of anthraquinone-1-sulfonic acid, anthraquinone-2-sulfonic acid, anthraquinone-2,6-disulfonic acid, anthraquinone-2,7-disulfonic acid, anthraquinone-1,5-disulfonic acid, 1,2-naphthoquinone-4-sulfonic acid, 1,4-benzoquinone-2-sulfonic acid, and 1,2-benzoquinone-4-sulfonic acid.

5. The electrolytic capacitor of claim 1, further comprising a liquid component,
    the liquid component including at least one compound selected from the group consisting of glycol compounds and glycerin compounds.

6. The electrolytic capacitor of claim 1, wherein the solid electrolyte layer is formed by impregnating a processing liquid containing the electrically conductive material and the additive, into at least part of the dielectric layer.

7. A manufacturing method of an electrolytic capacitor, the method comprising:
    a first step of preparing an electrically conductive material containing a π-conjugated polymer and a polymer dopant doped in the π-conjugated polymer and having a first anionic group;
    a second step of preparing a processing liquid containing the electrically conductive material and a quinone compound having a second anionic group; and
    a third step of forming a solid electrolyte layer by impregnating the processing liquid, into at least part of a dielectric layer of an anode body.

* * * * *